United States Patent [19]

Schmidt et al.

[11] 4,153,801

[45] May 8, 1979

[54] POLYETHERS HAVING TERMINAL AMINO GROUPS

[75] Inventors: Oskar Schmidt, Kittsee; Walter Sibral, Tulln, both of Austria

[73] Assignee: Lim Holding, S.A., Luxembourg, Luxembourg

[21] Appl. No.: 735,281

[22] Filed: Oct. 26, 1976

[30] Foreign Application Priority Data

| Oct. 27, 1975 [AT] | Austria | 8149/75 |
| Oct. 27, 1975 [AT] | Austria | 8152/75 |
| Oct. 27, 1975 [AT] | Austria | 8153/75 |
| Oct. 27, 1975 [AT] | Austria | 8154/75 |

[51] Int. Cl.$^2$ .................................. C07D 233/54
[52] U.S. Cl. ................................ 548/312; 544/296; 544/312; 548/310; 528/68
[58] Field of Search ................ 260/309.5; 548/312

[56] References Cited

U.S. PATENT DOCUMENTS

| 3,787,405 | 1/1974 | Porret et al. ............... 260/309.5 |
| 3,984,606 | 10/1976 | Morgan ..................... 260/309.5 |

*Primary Examiner*—Donald G. Daus
*Assistant Examiner*—James H. Turnipseed
*Attorney, Agent, or Firm*—Beveridge, DeGrandi, Kline & Lunsford

[57] ABSTRACT

The invention relates to novel poly(thio)ethers having terminal amino groups, a process for their production and their application in the production of polyureas showing increased thermal stability and improved tensile and structural strength.

11 Claims, No Drawings

POLYETHERS HAVING TERMINAL AMINO GROUPS

BACKGROUND OF THE INVENTION

It is known that polyureas possess a number of considerable advantages over polyurethanes of corresponding structure. Polyureas are obtained by reaction of polyisocyanates with polyamines. Suitable polyamines are particularly polyether polyamines of higher molecular weight. According to German Offenlegungsschrift No. 2 019 432, polyamines suitable for the production of such polyureas are obtained from aliphatic polyether polyols and isatic acid anhydride.

It was found that the use of polyether diamines having one of several heterocyclic nuclei (rings) in their molecule (center) leads to the obtention of polyureas which are far superior to those known in respect of thermal stability and tensile and structural strength.

The invention relates to novel compounds having terminal amino groups, said novel compounds being of the general formula

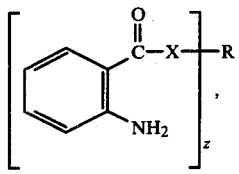
(I)

wherein z is 2 or 3, X stands for oxygen or sulfur and R is a z-valent group of the formula

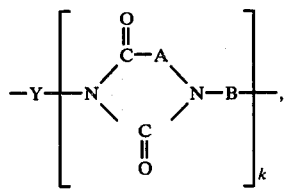
(II)

wherein k is 1 or 2, A stands for alkylidene or alkylated or non-alkylated vinylene, y stands for B when k=1 and z=2, for —CH$_2$— when k=2 and z=2 and for

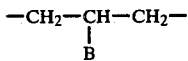

when k=2 and z=3, and B in each case represents a divalent polyalkylene ether group or a polyalkylene thioether group such as it is obtained by removal of the hydroxyl or mercapto group from a polyalkylene ether diol or a polyalkylene thioether dithiol of a molecular weight of 100 up to 15000. A further object of the invention is to provide a process for the production of these compounds. The production of the compounds of the present invention is advantageously effected by heating of a compound of the general formula (HX)$_z$R (general formula III) wherein z is 2 or 3 and R and X have the meaning defined above with at least z equivalents of isatic acid anhydride in the presence of strong bases to temperatures of 30° to 150° C., perferably to temperatures of 45° to 130° C. The reaction can be carried out with or without the presence of inert solvents. The amount of catalyst used can be varied within a wide range. Preferably, 1 to 10 parts by weight of the alkaline compound per 100 parts by weight of isatic acid anhydride are employed. The reaction is completed as soon as gas development ceases. The catalyst and excess isatic acid anhydride are filtered off, optionally after addition of an inert solvent, and the final product is obtained with a high degree of purity after treatment with CO$_2$, shaking with water and drying in vacuo under stirring. For the majority of application purposes, simple filtration of the amino polyether under pressure suffices.

Suitable starting materials for the process according to the invention are polyether diols and polyether triols as well as polythioether dithiols and polythioether triols and diols, triols, dithiols and trithiols comprising polyether segments or polythioether segments.

In the event that diols or dithiols (z=2) are used as starting materials in the process of the present invention, these could be chosen among the polyether diols or polythioether dithiols of the formula III having a molecular weight of about 100 to 15000, preferably 500 to 10000, in particular 500 to 3000, which are obtained by reaction of tetrahydrofurane or tetrahydrofurane and ethylene oxide or tetrahydrofurane and propylene oxide with a compound corresponding to the group R in formula II wherein B is hydrogen, CH$_2$CH$_2$OH or CH$_2$CH(CH$_3$)OH.

Preferred in the process according to the invention is the use of polymerisates of the formula III which are obtained by reacting ethylene oxide or propylene oxide or other 1,2-alkylene oxides or ethylene oxide and propylene oxide with a compound corresponding to R in formula II wherein B is hydrogen, CH$_2$CH$_2$OH or CH$_2$CH(CH$_3$)OH.

These compounds are produced according to conventional processes such as disclosed in German Offenlegungsschrift No. 2,003,016. Particularly preferred examples of the new compounds of the formula I obtained according to the process of the invention and having terminal amino groups are the following:

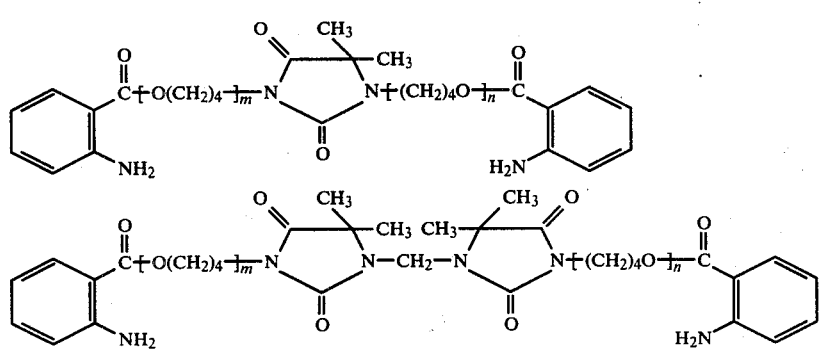

-continued
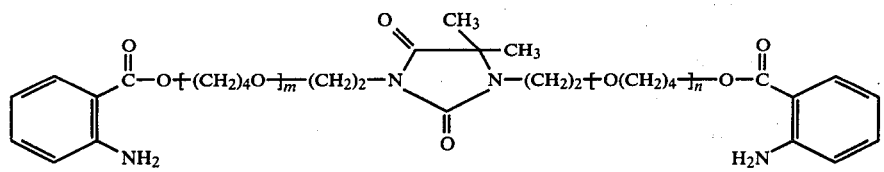 (3)
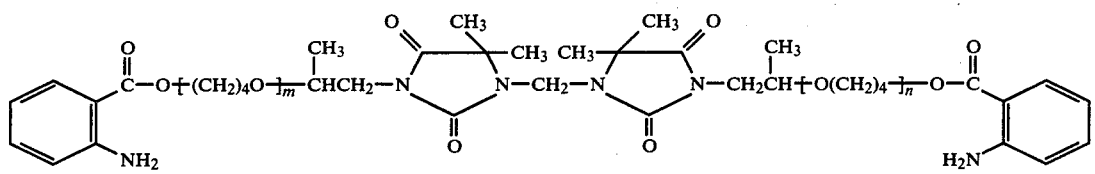 (4)
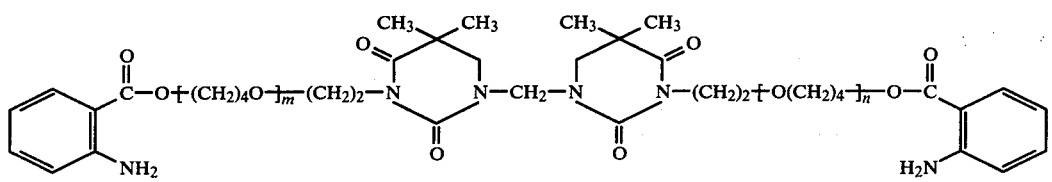 (5)
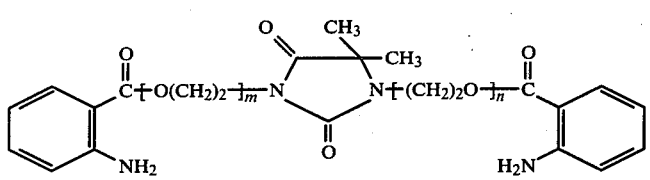 (6)
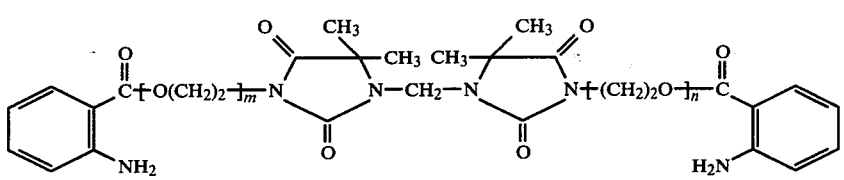 (7)
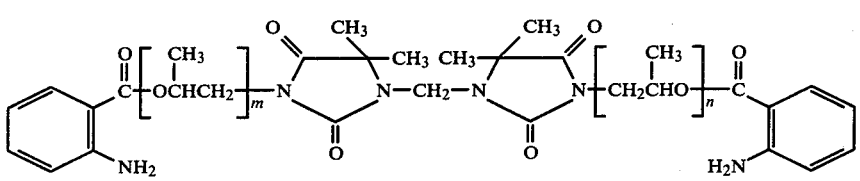 (8)
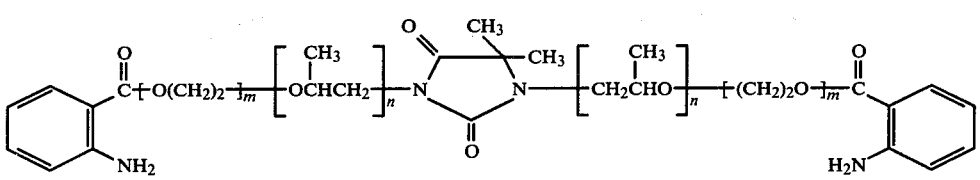 (9)
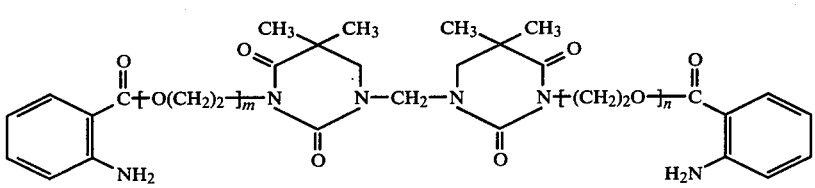 (10)
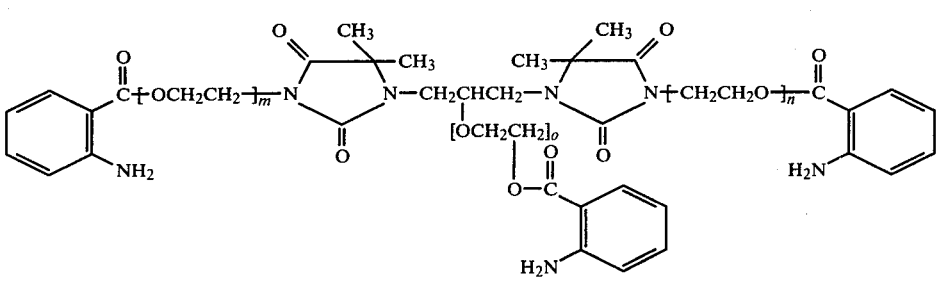 (11)

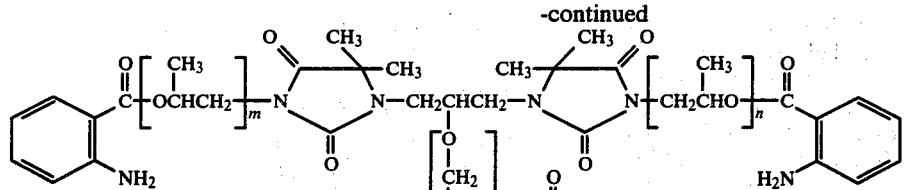

(12)

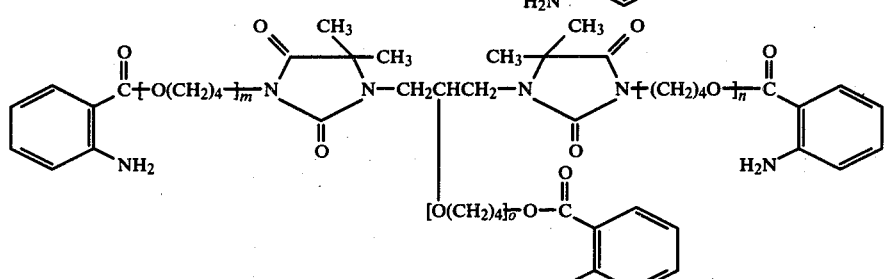

(13)

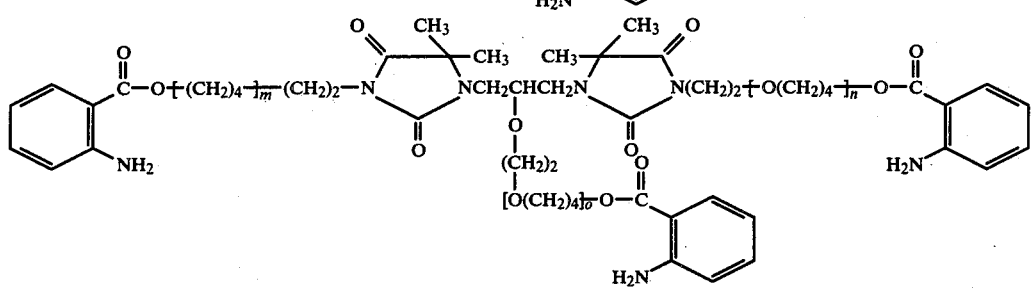

(14)

In these formulae of preferred compounds of the formula I, m, n and o in each case represent such integers that molecular weights of about 500 to about 15000, preferably of about 500 to about 3000 (when using diols or dithiols) and of about 800 to about 15000 (when employing triols or trithiols) are obtained in the compounds of the formula I.

In detail, compounds of the general formula I, their production and application are preferred in which A stands for an alkylidene group of 1 to 6 carbon atoms. Particularly obtainable among these are compounds of the formula I wherein A represents an isopropylidene group, an ethylidene group or a methyl vinylene group. B in the formula I can have the meaning of a polyethylene ether group, a polypropylene ether group or a polyalkylene ether group comprising ethylene ether groups and propylene ether groups in any given sequence.

The polyalkylene ether group can further contain ether groups as well as thioether groups.

Particularly preferred because of the ready availability of the starting materials and the properties of the end products are compounds of the formula I wherein B stands for a polyalkylene ether group derived from tetrahydrofurane, a polyalkylene ether group containing ethylene ether groups and alkylene ether groups derived from tetrahydrofurane in any given sequence or for a polyalkylene ether group containing alkylene ether groups derived from tetrahydrofurane and propylene ether groups, in any given sequence.

In the production of the new compounds of the formula I according to the present invention, it is thus preferred to use compounds of the general formula III wherein R represents a group of the formula II wherein A and/or B have one of the preferred meanings indicated above.

A further object of the present invention is the use or application of the compounds according to the invention or obtainable according to the process of the invention as reactants with polyisocyanate in the production of plastic materials according to the isocyanate polyaddition process.

The production of plastic materials from the new compounds according to the invention in the isocyanate polyaddition process can be effected in any given manner conventional in polyurethane chemistry, i.e. employed in the reaction of polyhydroxyl compounds with polyisocyanates. This means that the reaction of the new compounds with polyisocyanates can be carried out in the presence of all the additives known in polyurethane chemistry, such as catalysts, flame-retarding substances and the like.

In the production of elastomeric plastic materials of high modulus of elasticity, the polyadducts have preferably been obtained up to now in the presence of low molecular aromatic diamines as chain extenders. Since these diamines are carcinogenic, their use is encountering objections of a physiological nature. When employing the compounds according to the invention, the use of low molecular aromatic diamines can be completely omitted in the production of elastomeric plastic materials of high modulus of elasticity.

Suitable polyisocyanates for the production of polyadducts employing the new compounds of the present invention are all polyisocyanates known in polyurethane chemistry, such as, for instance, tetramethylene diisocyanate, hexamethylene diisocyanate, 2,4-diisocyanatotoluene, 2,6-diisocyanatotoluene, mixtures of these isomers, 4,4-diisocyanato diphenyl methane or the like.

As already mentioned, the polyadducts produced employing the new compounds according to the invention possess considerable advantages over polyurethanes of corresponding structure, particularly due to the increase in elasticity, stability and thermal stability.

The production of the compounds of the formula I is described in detail by means of the following Examples:

EXAMPLE 1

84.8 g (0.1 mol) of a compound of the formula

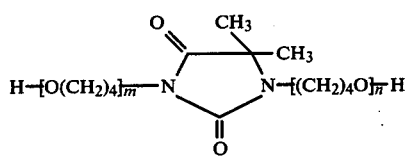

wherein m and n are integers, 35.9 g (0.22 mol) of isatic acid anhydride and 2.0 g powdered sodium hydroxide are heated for 3 hours to 80° C. and then briefly to 110° C.; after cooling, 100 ml methylene chloride are added and the mixture is filtered. For complete removal of the sodium hydroxide, 200 ml water are added to the filtrate and $CO_2$ is introduced. After three extractions with 200 ml water each, the organic phase is concentrated in vacuo. 105.5 g (97% of the theory) of a honey-coloured, viscous substance are obtained as residue.

Amine titration:

for 3.4734 g substance: 64 ml 0.1 n $HClO_4$ in glacial acetic acid.

EXAMPLE 2

51.2 g (0.1 mol) of a compound of the formula

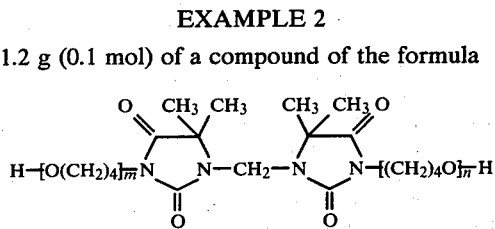

wherein m and n are integers, 35.9 g (0.22 mol) of isatic acid anhydride and 2.5 g powdered sodium hydroxide are reacted and treated as described in Example 1. This procedure yields 83.7 g (89% of the theory) of a yellow, highly viscous substance.

Amine titration:

for 1.2493 g substance: 26.6 ml 0.1 n $HClO_4$ in glacial acetic acid.

EXAMPLE 3

121.8 g (0.1 mol) of a compound of the formula

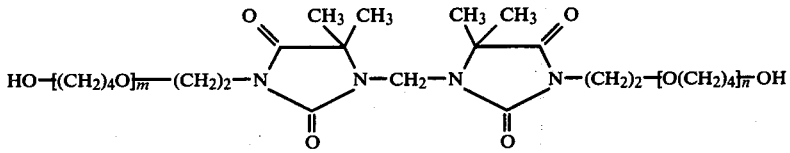

wherein m and n are integers, 35.9 g (0.22 mol) of isatic acid anhydride and 2.0 g powdered sodium hydroxide are heated for 3 hours to 90° C. and for 15 minutes to 120° C. and then treated according to Example 1. This procedure yields 138.5 g (95% of the theory) of a honey-coloured, viscous substance.

Amine titration:

for 1.4368 g substance: 19.9 ml 0.1 n $HClO_4$ in glacial acetic acid.

EXAMPLE 4

182.4 g (0.1 mol) of a compound of the formula

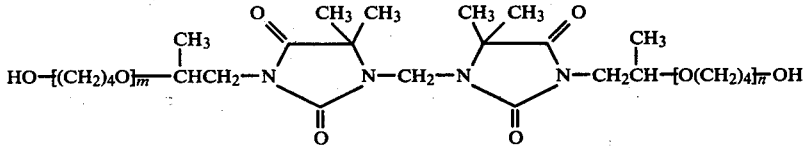

wherein m and n are integers, 35.9 g (0.22 mol) of isatic acid anhydride and 2.5 g powdered sodium hydroxide are heated for 4 hours to 100° C. and then treated according to Example 1. This yields 190 g (92% of the theory) of a honey-coloured, viscous substance.

Amine titration:

for 1.2763 g: 12.5 ml 0.1 n $HClO_4$ in glacial acetic acid.

EXAMPLE 5

124.4 g (0.1 mol) of a compound of the formula

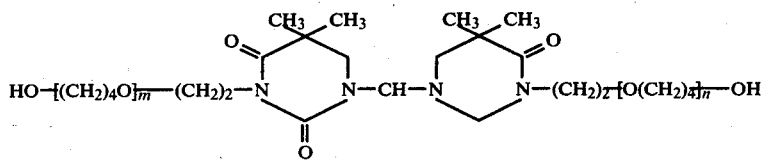

wherein m and n are integers, 35.9 g (0.22 mol) of isatic acid anhydride and 1.5 g powdered sodium hydroxide are heated for 3 hours to 75° C. and then for 1 hour to 110° C. and subsequently treated according to Example 1.

Amine titration:

for 1.7348 g substance: 23.5 ml 0.1 n $HClO_4$ in glacial acetic acid.

EXAMPLE 6

A mixture of 114.5 g (0.1 mol) of a compound of the formula

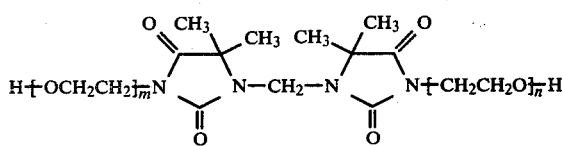

wherein m and n are integers, 35.89 g (0.22 mol) of isatic acid anhydride and 1.5 g powdered sodium hydroxide is heated for 3 hours to 90° C. and briefly to 120° C. and then cooled off. Then, 150 ml methylene chloride are added and the mixture is filtered. 300 ml water are added to the filtrate and $CO_2$ is introduced in order to completely remove the sodium hydroxide. After three extractions with 200 ml water each, the organic phase is concentrated in vacuo. This procedure yields 117.8 g (85% of the theory) of a honey-coloured, viscous substance.

Amine titration:
for 1.4023 g substance: 21 ml
0.1 n $HClO_4$ in glacial acetic acid.

EXAMPLE 7

100.5 g (0.05 mol) of a compound of the formula

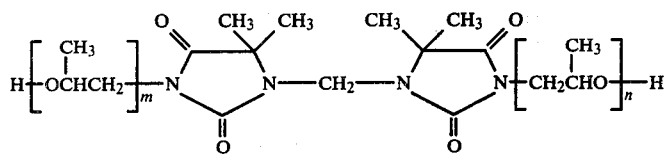

wherein m and n are integers, 18 g (0.11 mol) of isatic acid anhydride and 1 g powdered sodium hydroxide are heated to 100° C. for 4 hours and then treated according to Example 1. This yields 112 g (96% of the theory) of a yellow, viscous substance.

Amine titration:
for 2.7345 g substance: 24.5 ml
0.1 n $HClO_4$ in glacial acetic acid.

EXAMPLE 8

63.5 g (0.05 mol) of a compound of the formula

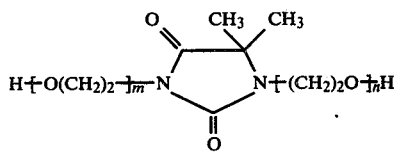

wherein m and n are integers, 18 g (0.11 mol) of isatic acid anhydride and 0.8 g powdered sodium hydroxide are reacted and treated according to Example 6. The yield amounts to 70.2 g (93% of the theory).

Amine titration:
for 1.3249 g substance: 17.7 ml
0.1 n $HClO_4$ in glacial acetic acid.

EXAMPLE 9

170 g (0.1 mol) of a compound of the formula

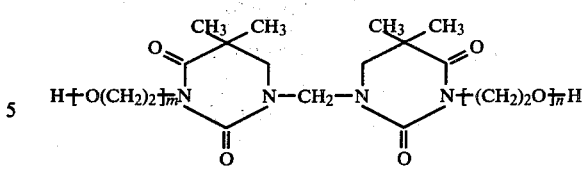

wherein m and n are integers, 35.9 g (0.22 mol) of isatic acid anhydride and 1.2 g powdered sodium hydroxide are heated together under stirring. The reaction starts at 70° C. and the temperature is raised to 110° C. in the end in order to complete it. Treatment according to Example 6 yields 190 g (98% of the theory).

Amine titration:
for 2.1365 g substance: 2.1 ml
0.1 n $HClO_4$ in glacial acetic acid.

EXAMPLE 10

996 g (0.1 mol) of a compound of the formula

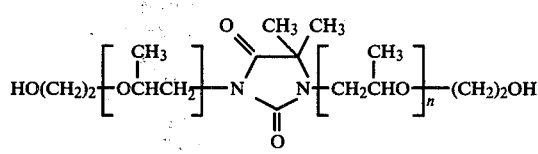

wherein n is an integer, 35.9 g (0.22 mol) of isatic acid anhydride and 7 g powdered sodium hydroxide are heated for 4 hours to 75° C., for 1 hour to 110° C. and then treated according to Example 6. The yield obtained amounts to 848 g (84% of the theory) of a viscous, honey-coloured substance.

Amine titration:
for 7.153 g substance:
13.3 ml
0.1 n $HClO_4$ in glacial acetic acid, (93.7% of the theory), which means that 93.7% of all OH-groups have reacted with isatic acid anhydride.

EXAMPLE 11

1400 g (0.1 mol) of a compound of the formula

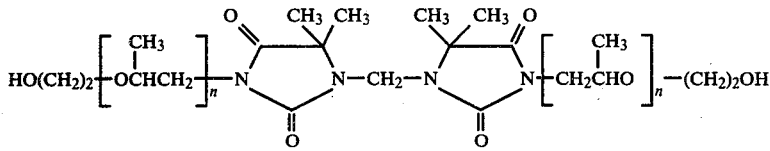

wherein n is an integer, 35.9 g (0.22 mol) of isatic acid anhydride and 10 g powdered sodium hydroxide are heated for 4 hours to 75° C. and for 1 hour to 100° C. and then treated in analogy to Example 1. This yields 1243 g (87% of the theory) of a viscous, honey-coloured substance.

Amine titration:
for 9.3158 g substance: 10.9 g
0.1 n $HClO_4$
in glacial acetic acid (83.9% of the theory).

EXAMPLE 12

214.4 g (0.1 mol) of a compound of the formula

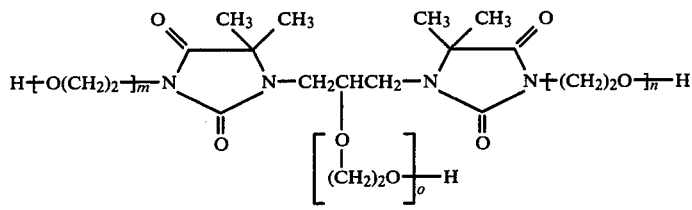

wherein m, n and o are integers, 57.4 g of isatic acid anhydride and 4.5 g sodium hydroxide are heated for 4 hours to 80° C. and for 30 minutes to 110° C. After cooling, 150 ml methylene chloride are added to the mixture and it is filtered. This is followed by the addition of 200 ml water to the filtrate and the introduction of $CO_2$ in order to completely remove the sodium hydroxide. After three extractions with 200 ml water each, the organic phase is concentrated in vacuo. The yield amounts to 235.1 g (94% of the theory) of a honey-coloured, viscous substance.
Amine titration:
for 1.2413 g substance: 15.0 ml
0.1 n $HClO_4$ in glacial acetic acid.

EXAMPLE 13

164.4 g (0.1 mol) of a compound of the formula

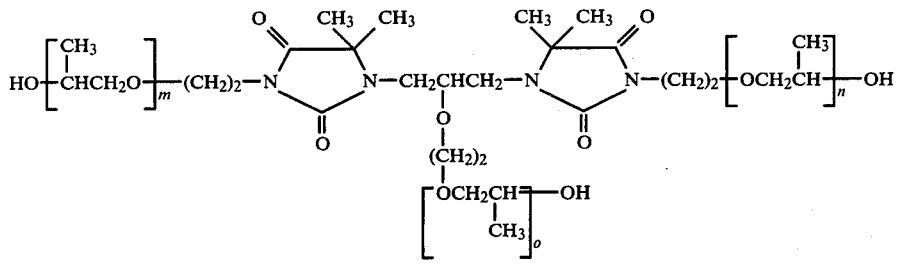

wherein m, n and o are integers, 57.4 g isatic acid anhydride and 4.0 g powdered sodium hydroxide are reacted and treated in analogy to Example 12. This yields 194.3 g (97% of the theory) of a honey-coloured, viscous substance.
Amine titration:
for 1.1686 g substance: 17.4 ml
0.1 n $HClO_4$ in glacial acetic acid.

EXAMPLE 14

221.4 g (0.1 mol) of a compound of the formula

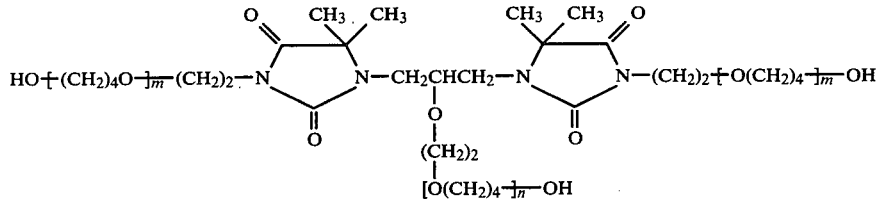

wherein m and n are integers, 57.4 g of isatic acid anhydride and 4.5 g powdered sodium hydroxide are heated for 1 hour to 80° C. and for 30 minutes to 110° C. After cooling, 150 ml methylene chloride are added to the mixture and it is filtered. This is followed by the addition of 200 ml water to the filtrate and the introduction of $CO_2$ in order to completely remove the sodium hydroxide. After three extractions with 200 ml water each, the organic phase is concentrated in vacuo. The yield amounts to 244.2 g (95% of the theory) of a honey-coloured, viscous substance.
Amine titration:
for 1.4271 g substance: 16.8 ml
0.1 n $HClO_4$ in glacial acetic acid.

The following Examples cover the application of the compounds according to the invention or obtainable according to the invention:

EXAMPLE 15

108.8 g (0.1 mol) of the diamine produced according to Example 1 and 18.5 g toluylene diisocyanate (80% 2,4-isomer, 20% 2,6-isomer) are mixed, poured into a mould and heated for 1 hour to 60° C. and for 24 hours to 100° C. This procedure yields an elastomer of excellent mechanical properties.
Tensile strength: 310 kp $cm^{-2}$
Structural strength: 50 kp $cm^{-1}$
Shore hardness DIN 53 505: 100

EXAMPLE 16

188.4 g (0.2 mol) of the diamine produced according to Example 2 and 37 g of the toluylene diisocyanate used in Example 15 are heated in a mould first for 30 minutes to 60° C. and then for 24 hours to 100° C. This yields an elastomer of excellent mechanical properties.
Tensile strength: 300 kp $cm^{-2}$
Structural strength: 50 kp $cm^{-1}$
Shore hardness DIN 53 505: 80

EXAMPLE 17

145.8 g (0.1 mol) of the diamine produced according to Example 3 and 18.5 g toluylene diisocyanate are heated in a mould first 30 minutes to 60° C. and then 24 hours to 100° C.

This yields an elastomer of excellent machanical properties.

Tensile strength: 270 kp cm$^{-2}$
Structural strength: 55 kp cm$^{-1}$ p Shore hardness: DIN 53 505: 75

EXAMPLE 18

151 g (0.1 mol) of the diamine produced according to Example 9 and 18.5 g of toluylene diisocyanate (80% 2,4-isomer, 20% 2,6-isomer) are mixed, poured into a mould and heated first for 1 hour to 60° C. and then for 24 hours to 100° C. This procedure yields an elastomer of excellent mechanical properties.

EXAMPLE 19

138.6 g (0.1 mol) of the diamine produced according to Example 6 and 18.5 g (0.106 mol) of the toluylene diisocyanate used according to Example 18 are heated in a mould first for 30 minutes to 60° C. and then for 24 hours to 100° C. An elastomer of excellent mechanical properties is obtained in this manner.

EXAMPLE 20

224.4 g (0.1 mol) of the diamine produced according to Example 7 and 18.5 g (0.105 mol) of the toluylene diisocyanate used according to Example 18 are heated in a mould first for 1 hour to 60° C. and then for 24 hours to 100° C. This procedure yields an elastomer of excellent mechanical properties.

EXAMPLE 21

194.0 g (0.1 mol) of the diamine employed according to Example 17 and 19.0 g of the toluylene diisocyanate used according to Example 18 are heated in a mould first for 30 minutes to 60° C. and then for 24 hours to 100° C. This procedure yields an elastomer of excellent mechanical properties.

EXAMPLE 22

92.4 g (0.066 mol) of the diamine produced according to Example 6 are reacted at 60° to 70° C. with 18.5 g toluylene diisocyanate. After 15 minutes, the temperature is raised to 90° C. under water jet vacuum. At this temperature, 5.9 g melted 1,4-dichloro-3,5-diaminobenzene are added to the mixture and it is poured into a preheated mould. This procedure yields an elastomer of excellent mechanical properties.

The tensile strengths of the elastomers produced according to Examples 18 to 22 ranged from 280 to 350 kp cm$^{-2}$, the structural strengths from 50 to 85 kp cm$^{-1}$ and the Shore hardnesses (DIN 53 505) from 58 to 96.

EXAMPLE 23

224 g (0.1 mol) of the diamine produced according to Example 7 are mixed with 42.5 g (0.245 mol) toluylene diisocyanate (80% 2,4-isomer, 20% 2,6-isomer) and stirred for one hour at 50°-60° C. The temperature is then raised to 90° C., 22.9 g of 1,4-dichloro-3,5-diaminobenzene are added and the mixture is poured into a mould. After heating for 24 hours, an elastomer of the following properties is obtained:

Tensile strength: 280 kp cm$^{-2}$
Structural strength: 48 kp cm$^{-1}$
Shore hardness DIN 53 505: 98

EXAMPLE 24

50 g (0.2 mol) of 4,4-diisocyanato diphenyl methane are added to 138.6 g (0.1 mol) of the diamine produced according to Example 6. After stirring for 1 hour at 80° C., 26.7 g (0.1 mol) of 1,4-dichloro-3,5-diaminobenzene heated to 120° C. are added to the mixture and it is poured into a mould. After heating for 24 hours, an elastomer of the following properties is obtained:

Tensile strength: 420 kp cm$^{-2}$
Structural strength: 85 kp cm$^{-1}$
Shore hardness DIN 53 505: 58

EXAMPLE 25

500.2 g (0.2 mol) of the triamine produced according to Example 12 and 55.7 g toluylene diisocyanate (80% 2,4-isomer, 20% 2,6-isomer) are mixed, poured into a mould and heated first for 1 hour to 60° C. and then for 24 hours to 100° C. This procedure yields an elastomer of excellent mechanical properties.

EXAMPLE 26

400.6 g (0.2 mol) of the triamine produced according to Example 13 and 55.7 g toluylene diisocyanate are heated in a mould first for one hours to 60° C. and then for 24 hours to 100° C. This procedure yields an elastomer of excellent mechanical properties.

EXAMPLE 27

514.2 g (0.2 mol) of the triamine produced according to Example 14 and 55.7 g toluylene diisocyanate (80% 2,4-isomer, 20% 2,6-isomer) are mixed, poured into a mould and heated for 1 hour to 60° C., then for 24 hours to 100° C. This procedure yields an elastomer of excellent mechanical properties.

What we claim is:

1. An imidazolidinedione compound of the formula

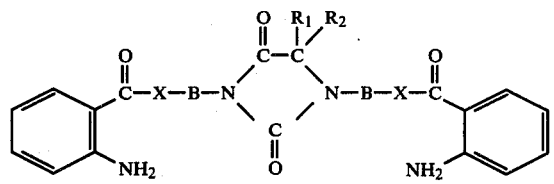

wherein:
R$_1$ and R$_2$ independently of one another represent hydrogen or methyl;
—X— is —O— or —S—;
—B— is bivalent polyalkylene ether or polyalkylenethio ether and said polyalkylene is a member selected from the group consisting of polyethylene, polypropylene, polybutylene, poly(ethylene-propylene), poly(ethylene-butylene) and poly(propylene-butylene) having a molecular weight of about 100 to 15,000.

2. A compound according to claim 1, wherein B represents a polyethylene ether group.

3. A compound according to claim 1, wherein B represents a polypropylene ether group.

4. A compound according to claim 1, wherein B represents a polyalkylene ether group containing ethylene ether groups and propylene ether groups in any given sequence.

5. A compound according to claim 1, wherein B represents a polyalkylene ether group derived from tetrahydrofurane.

6. A compound according to claim 1, wherein B represents a polyalkylene ether group containing ethylene ether groups and alkylene ether groups derived from tetrahydrofurane, in any given sequence.

7. A compound according to claim 1, wherein B represents a polyalkylene ether group containing propylene ether groups and alkylene ether groups derived from tetrahydrofurane, in any given sequence.

8. A compoud according to claim 1, represented by the formula (1)

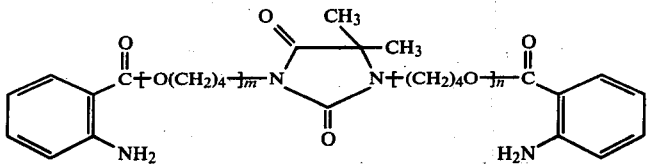

(1)

9. A compound according to claim 1, represented by the formula (3)

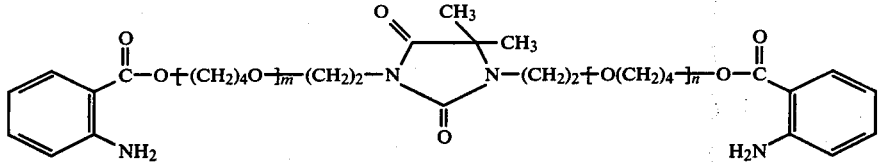

(3)

10. A compound according to claim 1, represented by the formula (6)

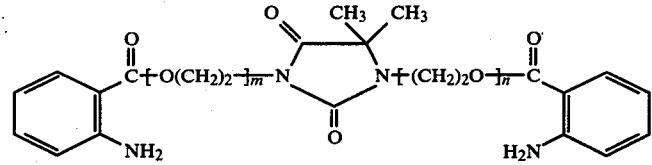

(6)

11. A compound according to claim 1, represented by the formula (9)

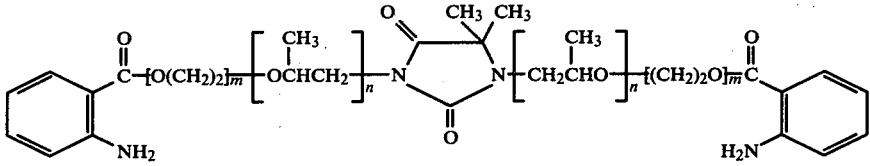

(9)

* * * * *